(12) United States Patent
Alzain

(10) Patent No.: US 10,314,672 B2
(45) Date of Patent: Jun. 11, 2019

(54) CHEEK AND TONGUE RETRACTOR

(71) Applicant: KING SAUD UNIVERSITY, Riyadh (SA)

(72) Inventor: Sahar Asaad Alzain, Riyadh (SA)

(73) Assignee: King Saud University, Riyadh (SA)

(*) Notice: Subject to any disclaimer, the term of this patent is extended or adjusted under 35 U.S.C. 154(b) by 0 days.

(21) Appl. No.: 15/801,222

(22) Filed: Nov. 1, 2017

(65) Prior Publication Data

US 2019/0125491 A1 May 2, 2019

(51) Int. Cl.
A61C 5/90 (2017.01)
A61B 13/00 (2006.01)
A61C 5/80 (2017.01)
A61B 1/24 (2006.01)

(52) U.S. Cl.
CPC ............. A61C 5/90 (2017.02); A61B 13/00 (2013.01); A61B 1/24 (2013.01); A61C 5/80 (2017.02)

(58) Field of Classification Search
CPC .... A61C 5/80; A61C 5/82; A61C 5/85; A61C 5/88; A61C 5/90; A61B 13/00; A61B 1/24
See application file for complete search history.

(56) References Cited

U.S. PATENT DOCUMENTS

| | | |
|---|---|---|
| 730,184 A | 6/1903 | Witter |
| 2,125,980 A | 8/1938 | Basil |
| 2,831,480 A | 4/1958 | Milano |
| 5,071,347 A | 12/1991 | McGuire |
| 5,503,556 A * | 4/1996 | Leonard ............. A61C 5/82 433/139 |
| 5,800,173 A * | 9/1998 | Heasley ............. A61C 5/90 433/136 |
| 5,890,899 A | 4/1999 | Sclafani |
| 6,213,772 B1 | 4/2001 | Costello |
| D491,663 S * | 6/2004 | Bat-Genstein ............. D24/176 |
| 6,939,134 B2 | 9/2005 | Sherry et al. |
| 2004/0209224 A1* | 10/2004 | Heasley ............. A61C 5/82 433/139 |

FOREIGN PATENT DOCUMENTS

CA 2298336 A1 8/2001

OTHER PUBLICATIONS

"Rubber Dam Clamps," Hu-Friedy website: https://www.hu-friedy.com/products/mastercontrol/index/file/id/32, © 2012.

* cited by examiner

Primary Examiner — Edward Moran
Assistant Examiner — Drew S Folgmann
(74) Attorney, Agent, or Firm — Richard C. Litman

(57) ABSTRACT

The retractor is a generally U-shaped device for protecting the cheek and tongue from instruments used during dental and prosthodontic procedures. The retractor has a planar base defined by two spaced arms, a pair of upright shields extending from the arms, and a posterior connector connecting the shields. The base is contoured to grip the tooth adjacent to the tooth to be treated, and thereby, secure the retractor within the patient's mouth.

5 Claims, 4 Drawing Sheets

CHEEK AND TONGUE RETRACTOR

BACKGROUND

1. Field

The disclosure of the present patent application relates to dental appliances, and particularly to a cheek and tongue retractor for restorative and prosthodontic treatment.

2. Description of the Related Art

During restorative dentistry and prosthodontic procedures, clinicians are often required to utilize carbide and/or diamond burs for drilling, finishing, and/or grinding at high speeds. To protect the tongue and cheek of the patient during these procedures, clinicians typically use cheek and tongue retractors. Many conventional retractors, however, include hinged joints, mirrors, and/or handles, which can block or minimize a work area in the mouth. Further, the clinician must grasp a retractor handle to maintain the retractor in a desired position during the procedure. As such, conventional retractors can also be difficult to use.

Thus, a cheek and tongue retractor for restorative and prosthodontic treatment solving the aforementioned problems is desired.

SUMMARY

The retractor is a generally U-shaped device for protecting the cheek and tongue from instruments used during dental and prosthodontic procedures. The retractor has a planar base defined by two spaced arms, a pair of upright shields extending from the arms, and a posterior connector connecting the shields. The base is contoured to grip the tooth adjacent to the tooth to be treated, and thereby, secure the retractor within the patient's mouth.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
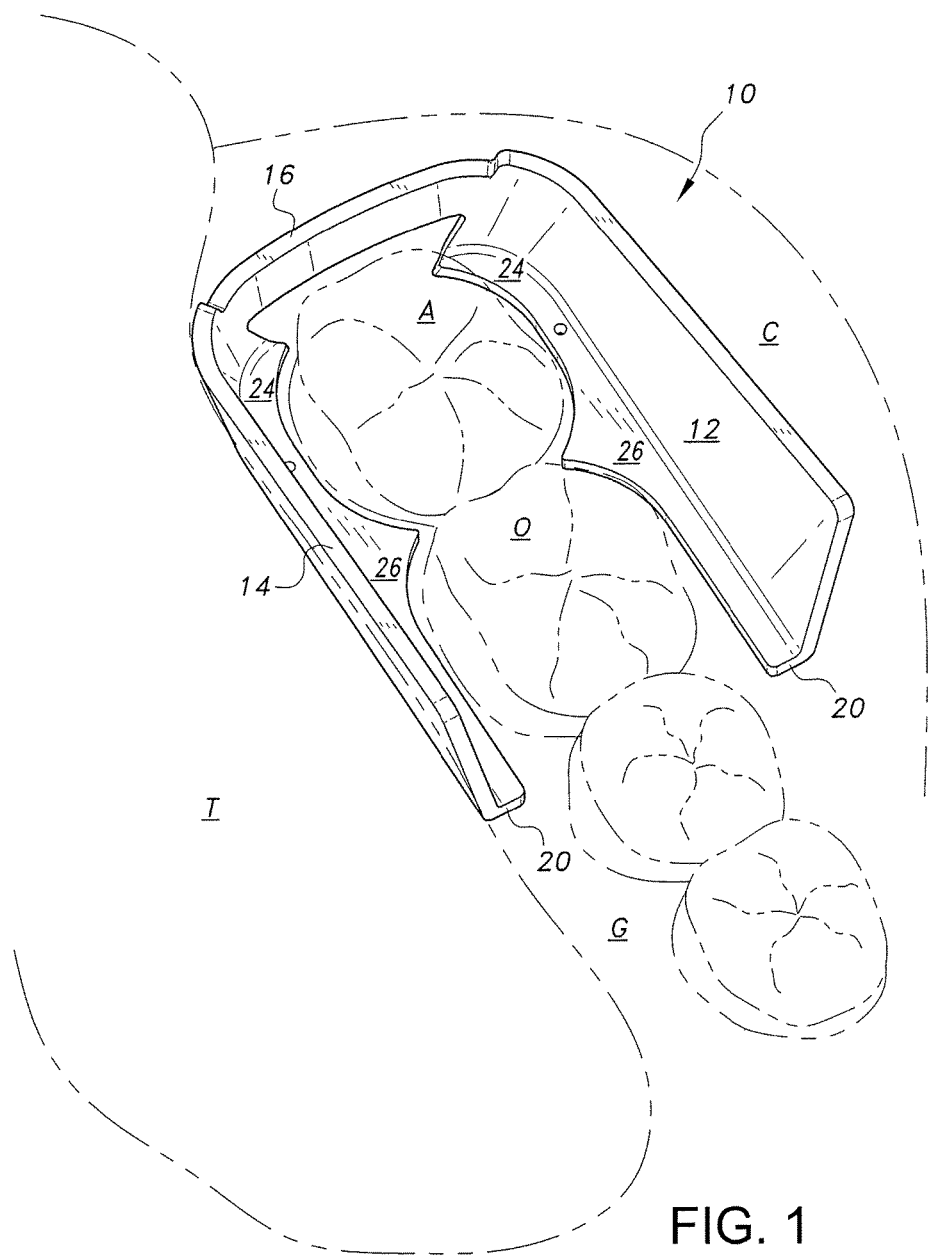
FIG. 1 is an environmental, perspective view of a cheek and tongue retractor for restorative and prosthodontic treatment.

The cheek and tongue retractor 10 can be used to protect the cheek and tongue from instruments used during dental and prosthodontic procedures. As is shown in FIGS. 1-6, the retractor 10 is a generally U-shaped device having a planar base 20, a buccal shield 12, a lingual shield 14, and a posterior connector 16 connecting the buccal shield 12 and the lingual shield 14. The base 20 is defined by a pair of spaced arms 40a, 40b. The buccal shield 12 and the lingual shield 14 extend generally upright from the arms 40a and 40b.

The base 20 is contoured to grip the tooth adjacent to the tooth to be treated, and thereby, secure the retractor 10 within the patient's mouth. Once secured to the adjacent tooth, the buccal shield 12 and the lingual shield 14 of the retractor 10 protect the cheek and tongue of the patient from instruments used during a procedure. It should be understood that the retractor 10 is self-retentive. In other words, an additional force is not required to hold the retractor 10 in place while a clinician is treating tooth O. Further, while the drawings show the buccal shield 12 adjacent to the cheek C and the lingual shield 14 adjacent to the tongue T, it should be understood that positioning the retractor 10 on an opposite side of the mouth can result in the buccal shield 12 being adjacent to the tongue T and the lingual shield 14 being adjacent to the cheek C.

Figure 2:
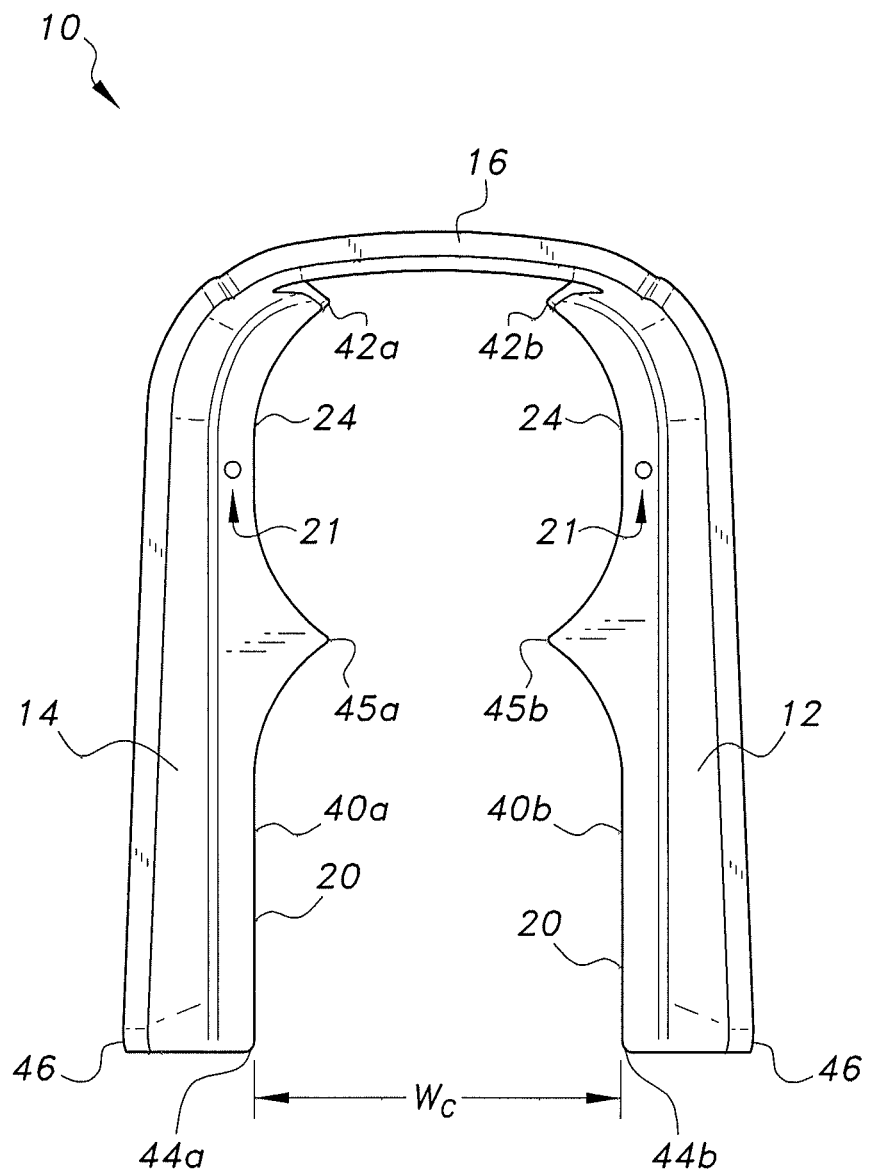
FIG. 2 is a plan view of the cheek and tongue retractor of FIG. 1.

As shown in FIGS. 1 and 2, the arms 40a, 40b of the base include curved first ends 42a, 42b, respectively, and opposing, straight second ends 44a, 44b, respectively. Arm 40a includes a generally V-shaped protrusion 45a extending between the first and second ends 42a, 44a toward arm 40b. Arm 40b includes a generally V-shaped protrusion 45b extending between the first and second ends 42b, 44b toward arm 40a. A base clasp portion 24 is defined by an area between the first curved ends and the protrusions of both of the arms 40a, 40b. A base frame portion 26 is defined by an area between the protrusions and the second ends of both of the arms 40a, 40b. The clasp portion 24 is configured for gripping the buccal and lingual undercuts of adjacent tooth A (the tooth adjacent to the tooth to be treated). The frame portion 26 is configured to extend along opposing sides of tooth O (the tooth to be treated). The base 20 can include apertures 21a, 21b, for receiving pins of forceps (not shown) or other tool which can be used to place the retractor in the mouth prior to a procedure.

Figure 3:
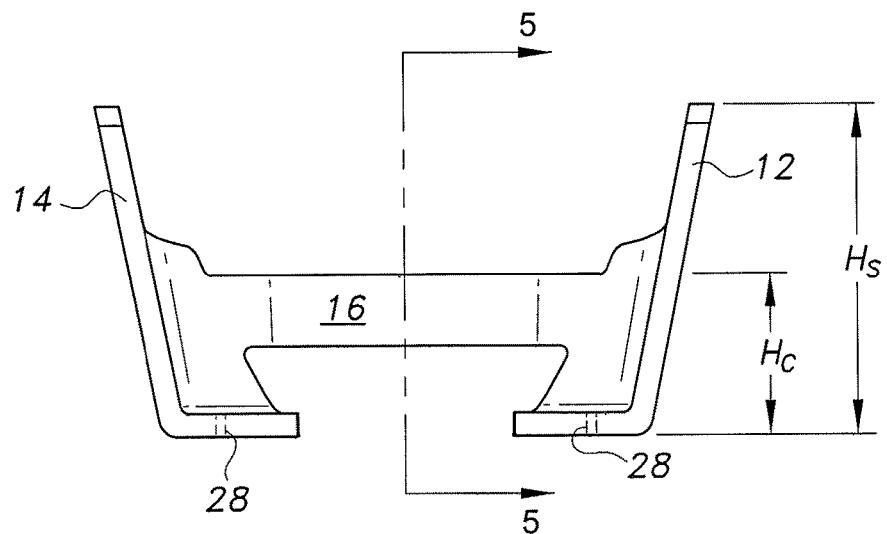
FIG. 3 is a front view of the cheek and tongue retractor of FIG. 1.
Figure 4:
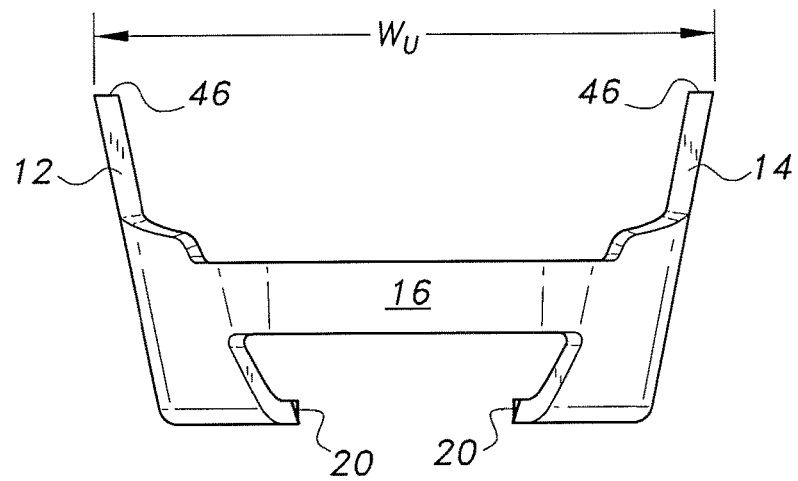
FIG. 4 is a rear view of the cheek and tongue retractor of FIG. 1.
Figure 5:
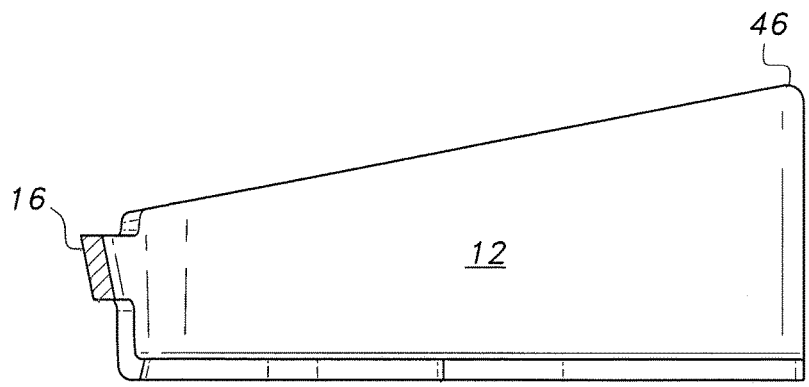
FIG. 5 is a section view drawn along lines 5-5 of FIG. 3.
Figure 6:
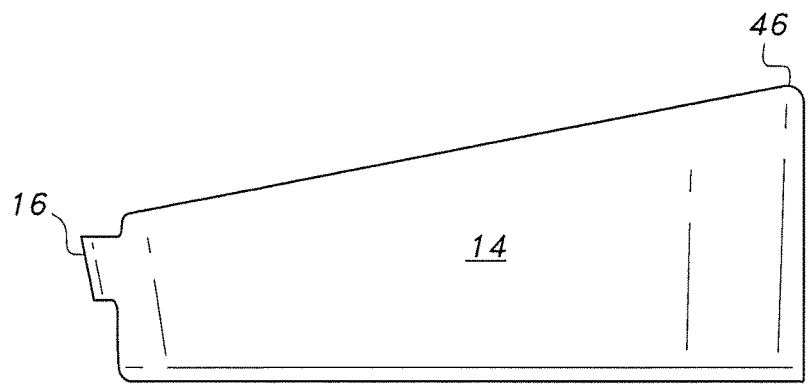
FIG. 6 is a left side view of the cheek and tongue retractor of FIG. 1.

In an exemplary embodiment, as shown in FIGS. 2-6, the distance $W_C$ between opposing second ends of the base is about 2.5 centimeters (FIG. 2). The distance $W_U$ between opposing ends of the two shields 12 and 14 is about 4.0 centimeters (FIG. 4). The height $H_S$ of each shield 12, 14 is about 2.5 centimeters, while the height $H_C$ of the connector is about 1.0 centimeter (FIG. 3). The height of the connector is preferably less than the height of the shields to avoid occlusal interferences between opposing teeth (FIGS. 5 and 6). It should be understood that the dimensions of the retractor 10 can vary depending on the size of the patient's teeth.

A clamp forceps can be used to place the retractor in the mouth of a patient. The pins of the clamp forceps can be inserted into apertures 20a, 20b. The clasp portion of the base 20 can then be positioned along buccal and lingual undercuts of the adjacent tooth A. Once the base 20 is secured to the adjacent tooth A, the forceps can be detached from the retractor.

The retractor 10 is preferably made from a resilient plastic or metal material. Preferably, the material can be sterilized in an autoclave without being distorted. The retractor parts can be rounded with smooth surfaces to avoid any possible tissue trauma.

It is to be understood that the cheek and tongue retractor for restorative and prosthodontic treatment is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A U-shaped cheek and tongue retractor adapted to clasp onto a tooth, consisting of:
    an elongated planar base having a longitudinal axis and including a pair of spaced apart arms, each of the arms having a curved first end, a straight second end thereby defining the U-shaped retractor, and a V-shaped protrusion extending laterally between the first end and the second end thereby forming a tooth engaging clasp portion adjacent the curved first end;
    a pair of upright, straight shields extending from the arms of the base and being coextensive therewith, each of the shields including a free first end and a second end, wherein the distance between the free ends of the shields is 4.0 cm and the distance between the arms of the base is 2.5 cm; and
    a posterior connector solely connecting the shields, wherein the connection is solely at the first end of the shields, further wherein the height of the posterior connector is 1.0 cm and the height of the shields is 2.5 cm thereby avoiding occlusal interference between opposing teeth.

2. The cheek and tongue retractor according to claim 1, wherein: each of the arms of the base include an aperture defined therethrough.

3. The cheek and tongue retractor according to claim 1, wherein the retractor is formed from a resilient material.

4. The cheek and tongue retractor according to claim 3, wherein the retractor is formed from a plastic material.

5. The cheek and tongue retractor according to claim 3, wherein the retractor is formed from a metal material.

* * * * *